United States Patent
Wu

(10) Patent No.: US 7,879,913 B2
(45) Date of Patent: Feb. 1, 2011

(54) IPTAKALIM HYDROCHLORIDE FOR DECREASING NICOTINE USE

(75) Inventor: Jie Wu, Avondale, AZ (US)

(73) Assignee: Catholic Healthcare West, San Francisco, CA (US)

( * ) Notice: Subject to any disclaimer, the term of this patent is extended or adjusted under 35 U.S.C. 154(b) by 906 days.

(21) Appl. No.: 11/168,156

(22) Filed: Jun. 28, 2005

(65) Prior Publication Data

US 2006/0293393 A1    Dec. 28, 2006

(51) Int. Cl.
*A01N 33/02* (2006.01)
*A01N 33/18* (2006.01)
*A01N 33/24* (2006.01)
*A61K 31/13* (2006.01)
*A61K 31/04* (2006.01)

(52) U.S. Cl. ...................... 514/663; 514/740
(58) Field of Classification Search ................. 514/663, 514/740
See application file for complete search history.

(56) References Cited

U.S. PATENT DOCUMENTS

| | | | |
|---|---|---|---|
| 4,255,439 A | 3/1981 | Cooper |
| 4,301,163 A | 11/1981 | Torossian et al. |
| 4,925,787 A | 5/1990 | Tanihara et al. |
| 4,956,388 A | 9/1990 | Robertson et al. |
| 5,021,457 A | 6/1991 | Akin et al. |
| 5,051,426 A | 9/1991 | Parnell |
| 5,132,402 A | 7/1992 | Tanihara et al. |
| 5,192,684 A | 3/1993 | Tanihara et al. |
| 5,219,858 A | 6/1993 | Parnell |
| 5,234,947 A * | 8/1993 | Cherksey ............... 514/449 |
| 5,250,571 A | 10/1993 | Fuller et al. |
| 5,369,028 A | 11/1994 | Harpold et al. |
| 5,371,188 A | 12/1994 | Heinemann et al. |
| 5,449,606 A | 9/1995 | Heinemann et al. |
| 5,574,052 A | 11/1996 | Rose et al. |
| 5,591,590 A | 1/1997 | Heinemann et al. |
| 5,683,912 A | 11/1997 | Elgoyhen et al. |
| 5,691,365 A | 11/1997 | Crooks et al. |
| 5,760,049 A | 6/1998 | Viner |
| 5,789,196 A | 8/1998 | Heineman et al. |
| 5,801,232 A | 9/1998 | Elliott et al. |
| 5,837,489 A | 11/1998 | Elliott et al. |
| 5,861,422 A | 1/1999 | Rose et al. |
| 5,910,582 A | 6/1999 | Elliott et al. |
| 5,935,975 A | 8/1999 | Rose et al. |
| 5,981,193 A | 11/1999 | Harpold et al. |
| 6,013,766 A | 1/2000 | Elgoyhen et al. |
| 6,022,704 A | 2/2000 | Elliott et al. |
| 6,083,962 A | 7/2000 | Rose et al. |
| 6,100,046 A | 8/2000 | Elgoyhen et al. |
| 6,136,550 A | 10/2000 | Heinemann et al. |
| 6,197,827 B1 | 3/2001 | Cary |
| 6,252,132 B1 | 6/2001 | Changeux et al. |
| 6,303,638 B1 | 10/2001 | Latli et al. |
| 6,303,753 B1 | 10/2001 | Elliott et al. |
| 6,323,000 B2 | 11/2001 | Briggs et al. |
| 6,455,754 B1 | 9/2002 | Changeux et al. |
| 6,485,967 B1 | 11/2002 | Elliott et al. |
| 6,524,789 B1 | 2/2003 | Elliott et al. |
| 6,562,847 B1 | 5/2003 | Lee |
| 6,646,109 B1 | 11/2003 | Elgoyhen et al. |
| 6,664,375 B2 | 12/2003 | Elliott et al. |
| 6,683,157 B2 | 1/2004 | Briggs et al. |
| 6,753,456 B2 | 6/2004 | Lester et al. |

OTHER PUBLICATIONS

Glover et al. American Journal of the Medical Sciences. Oct. 2003. vol. 326 , No. 4, pp. 183-186.*
Backer et al. Experientia. 1984. vol. 40, pp. 1363-1364.*
Shin et al. European Journal of Pharmacology. 2002. vol. 444, pp. 115-121.*
Milton et al. American Journal of Physiology Regulatory , Integrative and Comparative Physiology. Feb. 17, 2005, vol. 289, pp. R77-R83.*
Liu et al. Acta Pharmacologica Sinica, Jun 2003, vol. 24, No. 6, pp. 527-523 (or pp. 1-9 as provided).*
Cui, W., et al., "Effects of iptakalim hydrochloride on myocardial ATP-sensitive potassium channels", Chinese Pharm Bull, article, Feb. 2004, V 20; No. 2, pp. 166-171.
He, H., et al., "Effects of iptakalim hydrochloride on the association and dissociation kinetic processes of; 3H glibenclamide binding with ATP-sensitive potassium channels in artery smooth muscles and its crosstalk with nucleotides", Chinese Pharm Bull, article, Apr. 2004, V 20, Pt 4, pp. 402-408.

(Continued)

*Primary Examiner*—Sreeni Padmanabhan
*Assistant Examiner*—Samira Jean-Louis
(74) *Attorney, Agent, or Firm*—Joseph W. Mott

(57) ABSTRACT

A method for decreasing nicotine and other substance use in humans is disclosed. Iptakalim hydrochloride (IPT) is a novel nicotine acetylcholine receptor (nAChR) blocker. According to the disclosed method, IPT is used to block human α4β2-nAChR function. Specifically, IPT exhibits a selective blockade of α4 subunit-containing human nAChR subtypes. According to the disclosed method, IPT is thus used to block the major nicotine targets in the brain, the α4β2-nAChRs natively expressed in midbrain (VTA) DA system, the brain reward center, and in turn to reduce the nicotine-induced reward signals, namely dopamine level increase in nucleus accumbens. Therefore, IPT is capable of servicing as a nAChR antagonist agent and thus is a novel treatment for decreasing nicotine dependence in humans.

22 Claims, 11 Drawing Sheets

OTHER PUBLICATIONS

Jiang, Y., et al., "Effects of iptakalim hydrochloride on potassium currents in artery smooth muscles", Chinese Pharm Bull, article, May 2004, V 19; No. 5, pp. 540-547.

Liu, Y., et al., Ipticalim inhibits cocaine challenge-induced enhancement of dopamine levels in nucleus accumbens and striatum of rats by u-regulating Kir6.1 and Kir6.2 mRNA expression, Acta Pharmacol Sin, article, Jun. 2003, vol. 24, No. 6, pp. 527-533.

Long, C., et al., "Effects of iptakalim hydrochloride on hypertensive vascular remodeling", Chinese J Hypertension, article, Jun. 2003, V 11; No. 3, pp. 248-250.

Tang, X., et al. "The effect of the novel ATP-sensitive potassium channel opener, iptakalim hydrochloride on the glutamatergic neurotransmission and cocaine-induced motor activation", Soc for Neuroscience Abstract Viewer and Itinerary Planner, meeting, 32nd Annual Meeting of the Society for Neuroscience. vol. 2002, Nov 2-7, 2002, Abstract No. 36.1.

Wang, H., et al., "Targeting ischemic stroke with a novel opener of ATP-sensitive potassium channels in the brain", Mol Pharmacol, article, Nov. 2004, V 66, N 5, pp. 1160-1168.

Wang, H., "Pharmacological characteristics of the novel antihypertensive drug, iptakalim hydrochloride, and its molecular mechanisms", Drug Dev Res, article, V 58, N 1, Jan. 2003, pp. 65-68.

Xie, W., et al., "Effects of iptakalim hydrochloride, a novel KATP channel opener, on pulmonary vascular remodeling in hypoxic rats", Life Sci, article, V 75, N 17, Sep. 10, 2004, pp. 2065-2076.

Yang, Y., et al., "Effects of iptakalim on rotenone-induced cytotoxicity and dopamine release from PC12 cells", Neurosci Lett, article, Aug. 5, 2004, vol. 366, N 1, pp. 53-57.

Zhang, C., et al., "Synthesis of (N-; 2H.7) iptakalim hydrochloride and its proposed fragment pathways of mass spectroscopy", Chinese J Medicinal Chem, article, V 14, Pt 3, Ju.

Zhang, C., et al., "Synthesis of 2H- and 3H-labelled iptakalim hydrochloride", J Labeled Compounds and Radiopharmaceuticals, article, V 47, N 9, Aug. 2004, pp. 583-590.

Zhang, Y., et al., "Effects of iptakalim hydrochloride on cerebral neuronal sodium, calcium and potassium channels", Chinese Pharm Bull, article, May 2004, V 20; Pt 5, pp. 532-.

Zhu, Q., et al., "The effect of iptakalim hydrochloride on hemodynamics in anaesthetized normotensive dogs", Chinese J New Drugs, article, V 12, N 11, 2003, pp. 906-909.

Misaki, et al, "Iptakalim, a Vascular ATP-Sensitive Potassium Channel Opener . . .", JPET 322:871-878, 2007, Am Soc. Pharmacology and Experimental Therapeutics.

Wu, et al, "Iptakalim Modulates ATP-Sensitive K+ Channels . . ." JPET 319:155-164, 2006, Am Soc. Pharmacology and Experimental Therapeutics.

Avshalumov, et al, "Activation of ATP-Sensitive K+ Channels by H202 . . .", Proc Nat Acad Sci USA 100:11729-11734, 2003, Nat Acad of Sciences of the USA.

Milton, et al, "Adenosine and ATP-Sensitive Potassium Channels Modulate Dopamine Release" Am J Physiol Regul Integr Comp Physiol 289:77-83, 2005, Am Physiol Soc.

Barik, et al, "Molecular and Cellular Mechanisms of Action of Nicotine in the CNS," Nicotine Psychopharm. p. 173-207 (J.E. Henningfield ed 2009), Springer-Verlag (Pub) Berlin.

Dwoskin, et al, "Nicotinic receptor-based therapeutics and candidates for smoking cessation", Biochem Pharmacol, 2009, Elsevier, Inc.

* cited by examiner

FIG. 1 Iptakalim hydrochloride

FIG. 3
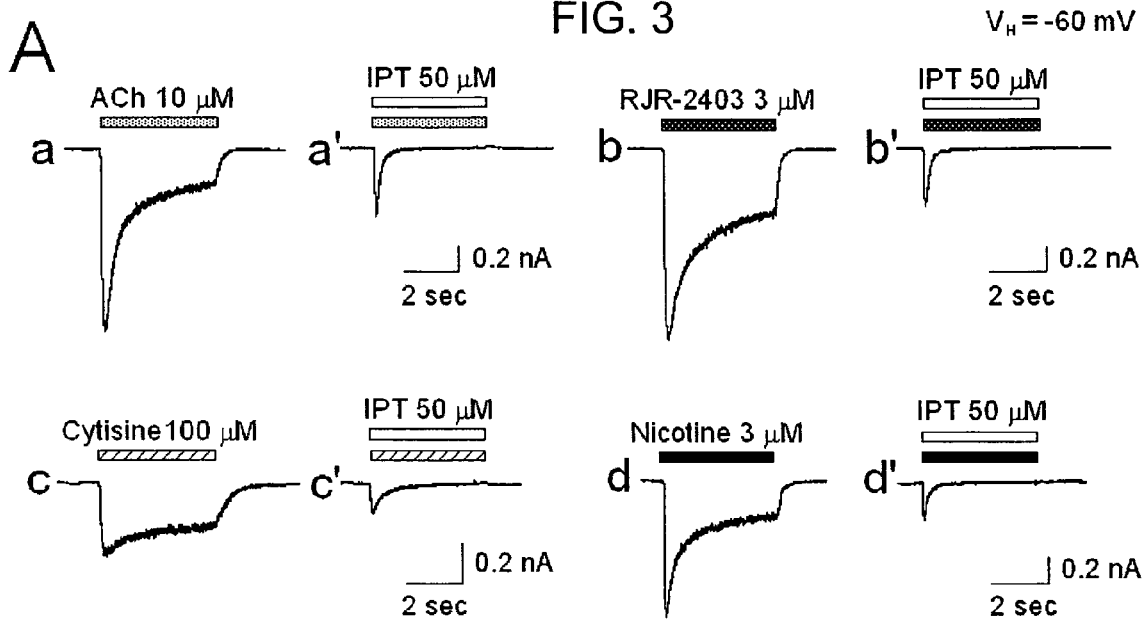
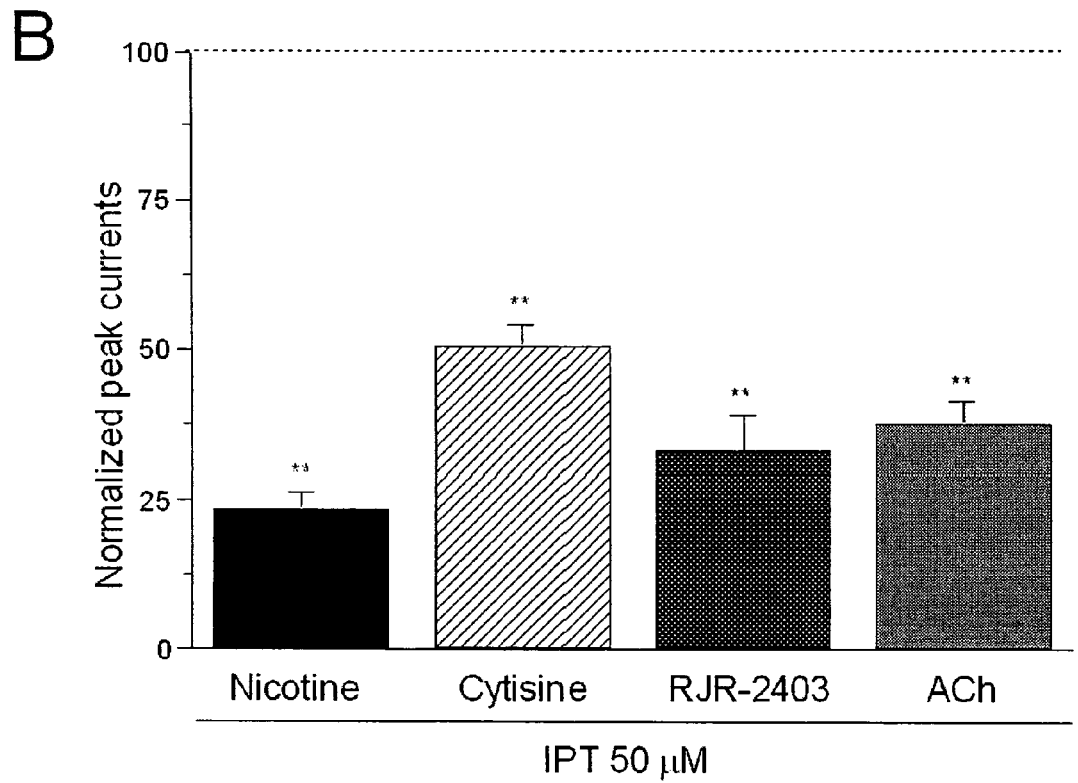

FIG. 7
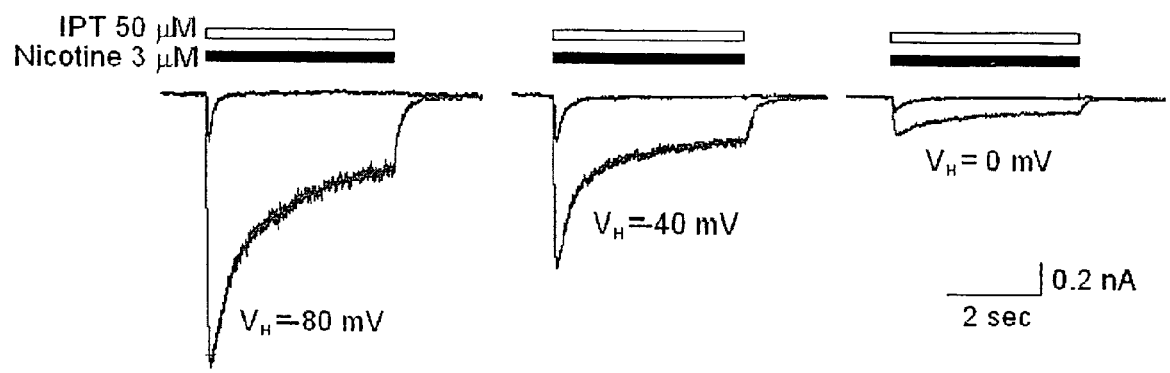
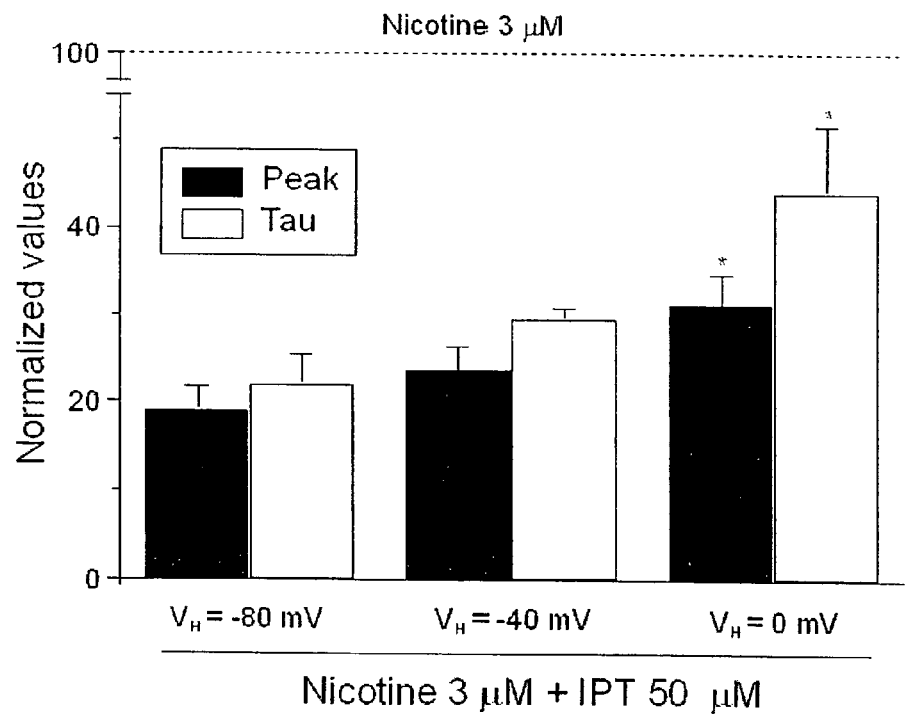

FIG. 8
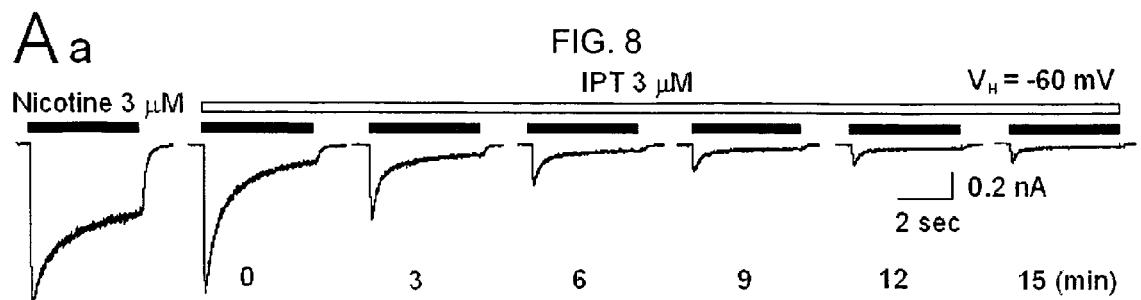
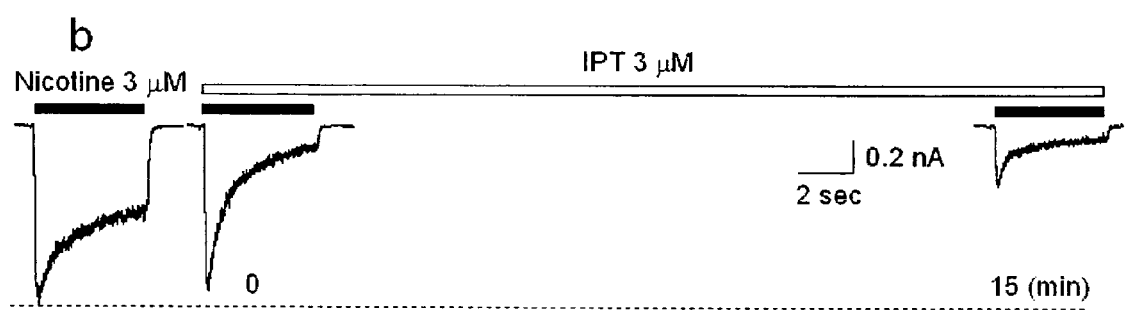
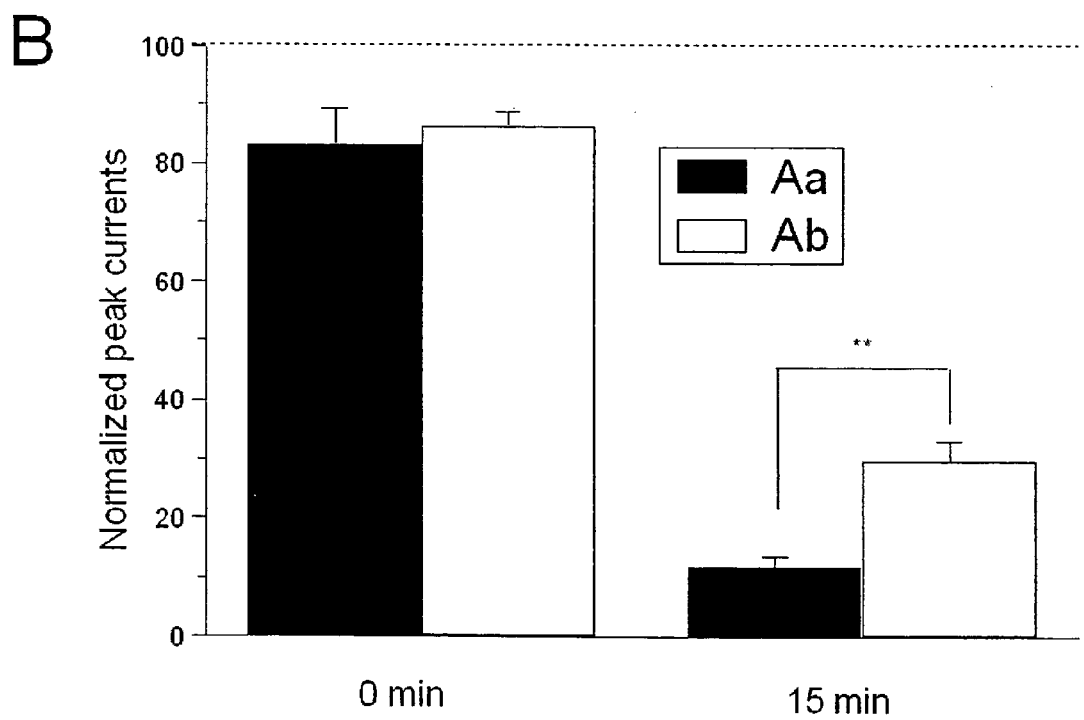

IPTAKALIM HYDROCHLORIDE FOR DECREASING NICOTINE USE

FIELD OF THE INVENTION

The present invention relates generally to a novel method for decreasing a human's cravings for cigarettes and reducing instances of relapse during detoxification once smoking abstinence has been achieved, and more specifically, to a method for decreasing nicotine use by treating a human with a novel type of nicotinic acetylcholine receptor antagonist, iptakalim hydrochloride (IPT).

BACKGROUND OF THE INVENTION

Cigarette smoking is a prevalent, modifiable risk factor for increased morbidity and mortality in the United States, and perhaps in the world. Smokers incur medical risks attributable to direct inhalation. Bystanders, termed passive smokers, also incur medical risks from second-hand smoke. Society, as a whole, also bears the economic costs associated with death and disease attributable to smoking. Although the majority of smokers have tried repeatedly to quit smoking, eighty percent of smokers return to tobacco in less than two years after quitting. Therefore, tobacco dependence is a health hazard for millions of Americans.

Nicotine is the biologically active substance that is thought to promote the use of tobacco products by approximately one-quarter of the world populations. Tobacco-related disease is personally and economically costly to the any nation. Unfortunately, once use of tobacco has begun, it is hard for a smoker to quit because of nicotinic dependence and addiction.

The initiation and maintenance of tobacco dependence in a human is due to certain bio-behavioral and neuromolecular mechanisms. Nicotinic acetylcholine receptors (nAChRs) in humans are the initial binding sites for nicotine. The binding of nicotine to nAChRs is thought to modulate the brain's "reward" function by triggering dopamine release in the human brain. The nAChRs exist as a diverse family of molecules composed of different combinations of subunits derived from at least sixteen genes. nAChRs are prototypical members of the ligand-gated ion channel superfamily of neurotransmitter receptors. nAChRs represent both classical and contemporary models for the establishment of concepts pertaining to mechanisms of drug action, synaptic transmission, and structure and function of transmembrane signaling molecules.

Basic cellular mechanisms of nicotinic dependence also involve the functional state changes during repeated nicotinic agonists exposure and receptor changes in the number of receptors during chronic nicotinic exposure. nAChRs can exist in many different functional states, such as resting, activated, desensitized or inactivated The activation and/or desensitization of nAChRs plays an important role in initiating nicotinic tolerance and dependence. Recovery from receptor activation and/or desensitization contributes to nicotinic withdrawal symptoms.

The most abundant form of nAChRs in the brain contains $\alpha 4$ and $\beta 2$ subunits. $\alpha 4\beta 2$-nAChRs bind nicotine with high affinity and respond to levels of nicotine found in the plasma of smokers. $\alpha 4\beta 2$-nAChR also have been implicated in nicotine self-administration, reward, and dependence. Therefore, selective drug action at nAChRs, especially at those containing $\alpha 4$ subunits, is thought to be an ideal way for nicotine cessation and reducing nicotine withdrawal syndrome. Unfortunately, thus far, no optimal compound can meet this purpose. The brain-blood-barrier permeable nAChR antagonist, mecamylamine is popularly used systemically but exhibits much less nAChR subtype selectivity.

Although a variety of psychopharmacological effects contribute to drug reinforcement, actions on the mesolimbic dopaminergic pathway is the predominant hypothesis for mechanisms of nicotinic reward. The mesolimbic dopaminergic pathway originates in the ventral tegmental area (VTA) of the midbrain and projects to forebrain structures including the prefrontal cortex and to limbic areas such as the olfactory tubercle, the amygdala, the septal region, and the nucleus accumbens. Many studies have indicated that dopamine release in the nucleus accumbens of the human brain is "rewarding" or signals an encounter with a "reward" from the environment. Other substances, such as alcohol, cocaine, and opiates, operate in the same manner, resulting in a cycle of substance or alcohol abuse.

Therefore, a considerable need exists for a novel compound that can selectively block $\alpha 4$ subtypes of nAChRs to prevent smoking-induced "reward", to limit increasing nicotine-induced dopamine release, and/or to diminish nicotinic withdrawal symptoms.

BRIEF DESCRIPTION OF THE DRAWINGS

FIG. 3 shows that IPT inhibits human $\alpha 4\beta 2$-nAChR function activated by different nicotinic agonists.

FIG. 7 shows that IPT inhibits nicotinic responses in a voltage-dependent manner.

FIG. 8 illustrates that IPT inhibits nicotinic responses in a use-dependent manner.

SUMMARY OF THE INVENTION

A method for decreasing nicotine use in humans is disclosed. Iptakalim hydrochloride (IPT) is a novel nicotine acetylcholine receptor (nAChR) blocker. According to the disclosed method, IPT is used to block human $\alpha 4\beta 2$-nAChR function. Specifically, IPT exhibits a selective modulation of human $\alpha 4$ nAChR subtypes.

The $\alpha 4\beta 2$-nAChRs, natively expressed in the midbrain (VTA) DA system, which is the brain's reward center, are major nicotine targets. Therefore, IPT serves as a novel nAChR antagonist to decrease nicotine-stimulated dopamine release and to decrease nicotine dependence in humans.

Finally, because IPT can also be used as a nAChR antagonist to block brain nAChR functions that do not involve the brain reward center, IPT can be used to prevent and/or diminish nicotine cessation-induced withdrawal symptoms.

DETAILED DESCRIPTION

Other independent features and advantages of the method for decreasing nicotine use in living organisms will become apparent from the following detailed description, taken in conjunction with the accompanying drawings which illustrate, by way of example, the principles of the invention.

DETAILED DESCRIPTION

Figure 1:
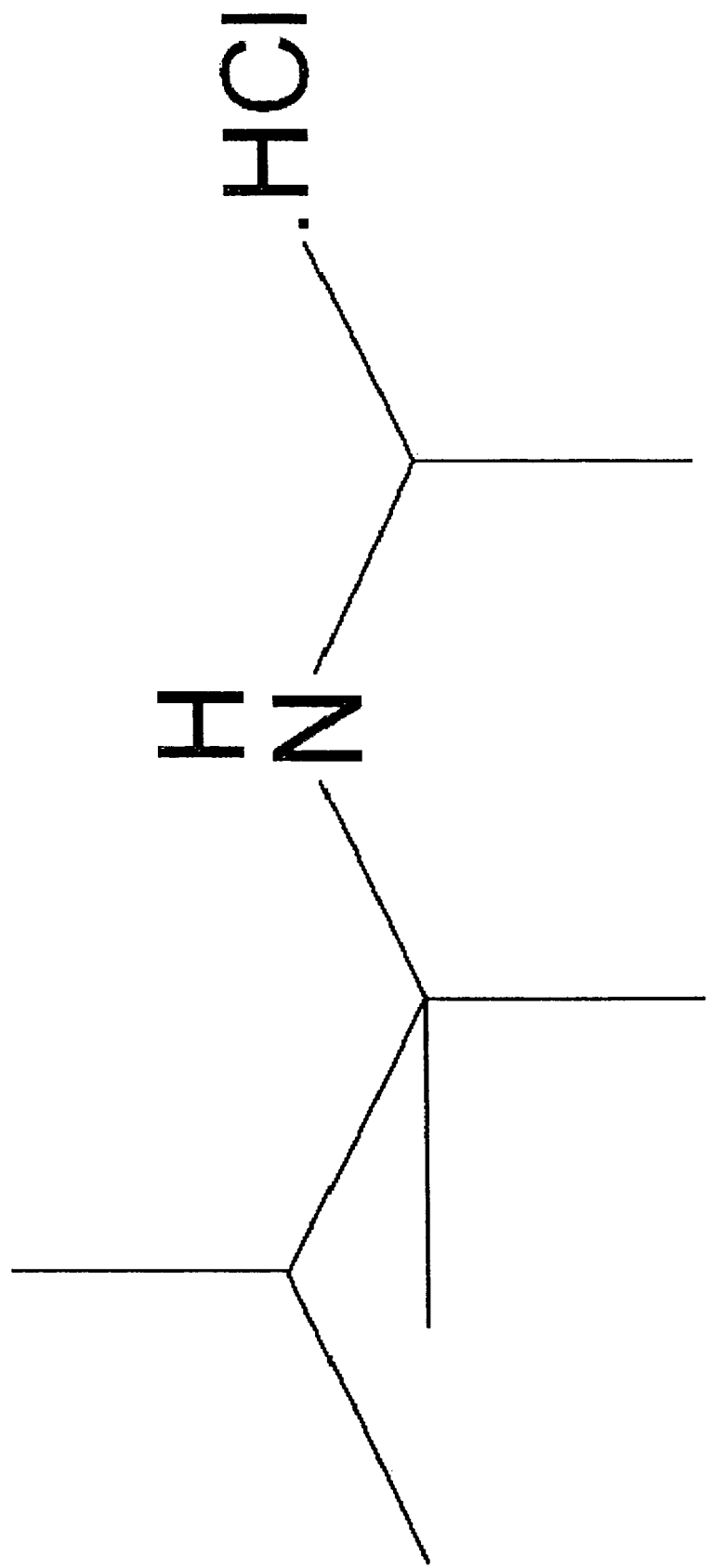
FIG. 1 shows the chemical structure of iptakalim hydrochloride.

This description discloses a method for reducing smoking in humans by treating a human with iptakalim hydrochloride (IPT). FIG. 1 shows the chemical structure of IPT.

IPT was initially designed and synthesized as a novel antihypertensive drug with some advantageous properties such as brain-blood-barrier penetrability, water solubility and a low side effect profile in vivo in animal studies. However, the roles of IPT in human nAChR function have been entirely unknown. The present disclosure shows that IPT is a novel nAChR blocker, more selective for the α4-nAChR subtype, and thus has utility as a treatment for reducing smoking and other nicotine use in humans.

Heterologously expressed, human α4β2-nAChRs in cloned human epithelia cell (SH-EP1 cell line) were employed as a cellular model to test IPT's pharmacology. IPT acts as a potent and selective antagonist of α4-containing nAChR. IPT inhibits both peak and steady-state whole-cell current responses to nicotinic agonists and accelerates acute desensitization in a concentration-dependent manner while having long-lasting effects after washout. Its effects are enhanced by exposure to nAChR prior to agonist challenge.

Use and voltage dependence of its effects at α4β2-nAChR, as well as its inability to block binding of $^3$H-ebibatidine, teach against a competitive mechanism of functional blockade and teach toward non-competitive interaction with α4β2-nAChR. Actions of IPT are nAChR subtype-selective, in that it is more potent as an antagonist of α4β2- or α4β4-nAChR than of α7-nAChR, and its effects are longer lasting at α4β2- than at α4β4-nAChR. Further, pretreatment with IPT induced more profound inhibition of the nicotinic response, suggesting that IPT binding sites are at least partially accessible in the resting state.

Figure 2:
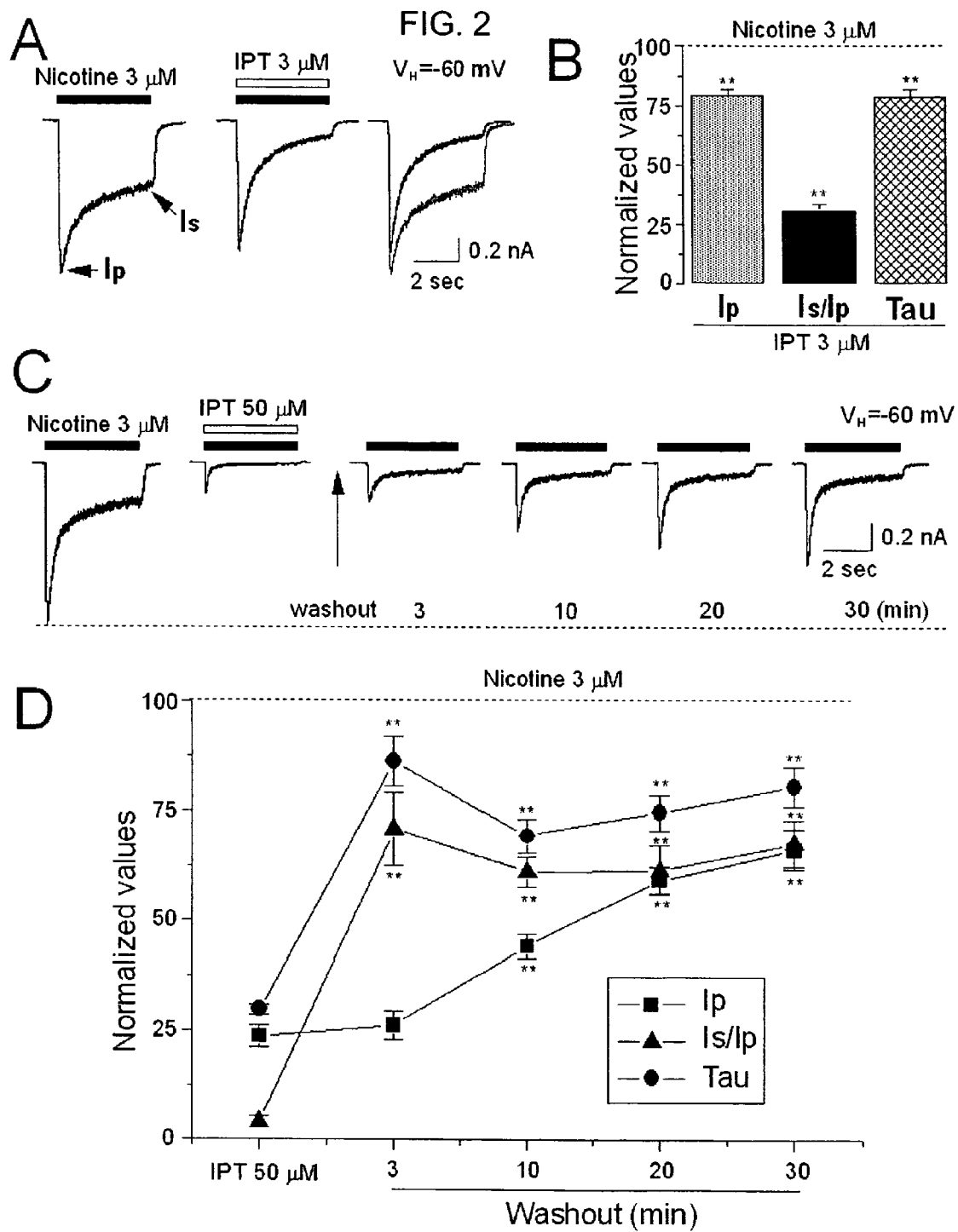
FIG. 2 shows that IPT inhibits heterologously-expressed, human $\alpha 4\beta 2$-nAChR-mediated whole-cell currents.

As shown in FIG. 2, relative to stable whole-cell current responses elicited during challenge exposure to 3 µM nicotine alone, nicotine-induced inward currents mediated via human α4β2-nAChRs in the same cell were reduced if assessed during co-application with 3 µM IPT. FIG. 2A illustrates that under whole-cell voltage-clamp recording conditions, rapid application of 3 µM nicotine through a U-tube to the recorded cell induced an inward current consisting of peak (Ip) and steady-state (Is) components (left trace).

Co-application of 3 µM IPT and nicotine reduced both peak and steady-state current components and accelerated the decay from the peak to the steady-state current (middle trace). The whole-cell traces of nicotinic responses with and without IPT are superimposed in the right traces. For these and all subsequent traces, current amplitude and time calibration bars are indicated, the holding potential ($v_H$) was −60 mV unless indicated otherwise, and the duration of ligand exposure is indicated by the bars above the trace.

In the presence of 3 µM IPT, both peak (20.85±2.69%, n=6) and steady-state components were reduced. The ratio of steady-state to peak current was reduced by 68.62±2.23% (n=6), and the rate of decay from peak to steady-state current was accelerated by 21.38±3.40% (n=6). Statistical analysis in FIG. 2B shows that 3 µM IPT exposure significantly inhibits α4β2-nAChR function. α4β2-nAChR function is represented here as peak whole-cell current (Ip, shaded bar), the ratio between peak and steady-state currents (Is/Ip, solid bar), and the decay constant (Tau, stippled bar) for the decline in inward current from peak to steady-state levels. In this and all following figures, unless specifically mentioned, each column (or symbol) is the average from 4-6 cells tested, and vertical bars indicate±standard error. A single asterisk (*) represents p<0.05, and double asterisks (**) represent p<0.01 compared to the parameter for responses to 3 µM nicotine (horizontal dashed line).

Brief (4 sec) exposure to IPT (50 µM) caused long-lasting effects on α4β2-nAChR function. FIG. 2C illustrates the time-dependence for recovery of α4β2-nAChR function from IPT inhibition after a brief exposure (4 sec) and washout for the indicated period (min) for responses to 3 µM nicotine.

For example, the half-time for recovery of peak current response to nicotine challenge was ~15 min, although effects on steady-state inward current levels and on the time constant for current decay recovered more quickly. FIG. 2D normalized values (±SE; n=4-6 cells) for the indicated parameters (peak current, Ip, ■; steady-state:peak current ratio, Is/Ip, ▲; decay constant, Tau, ●; ordinate) are plotted against the time of washout of 50 µM IPT (abscissa, min) for responses to 3 µM nicotine. The horizontal dashed line at 100% represents the value for the parameters for responses to 3 µM nicotine before exposure to IPT. A double asterisk (**) represents p<0.01 compared to 50 µM IPT-induced inhibition.

Turning now to FIG. 3, IPT (50 µM) also acts as an antagonist of ACh-, RJR-2403-, or cytisine-induced whole-cell currents mediated via heterologously expressed human α4β2-nAChRs. As shown in FIG. 3A, traces a-d show typical inward current responses induced by different nAChR agonists (drug identities, doses and treatment times are indicated by labels and horizontal bars above each trace) and recorded from different cells, and effects of 50 µM IPT co-applied with agonist are shown in traces a'-d'. Effects of 50 µM IPT on α4β2-nAChR-mediated peak whole-cell currents are shown for responses to the indicated agonists and normalized to the response to 3 µM nicotine in the absence of IPT. Results are averages±SE for records from 6 cells. A double asterisk (**) represents p<0.01 compared to a 3 µM nicotine-induced current.

In the presence of $EC_{50}$ concentrations of ACh (10 µM), RJR-2403 (3 µM), or nicotine (3 µM), 50 µM IPT produced 65.81±1.49%, 72.72±1.98% and 76.37±2.56% block of peak whole-cell currents, respectively. 50 µM IPT produced 49.32±3.46% block of responses to cytisine (100 µM) at a maximally efficacious concentration of this partial agonist at α4β2-nAChR.

Figure 4:
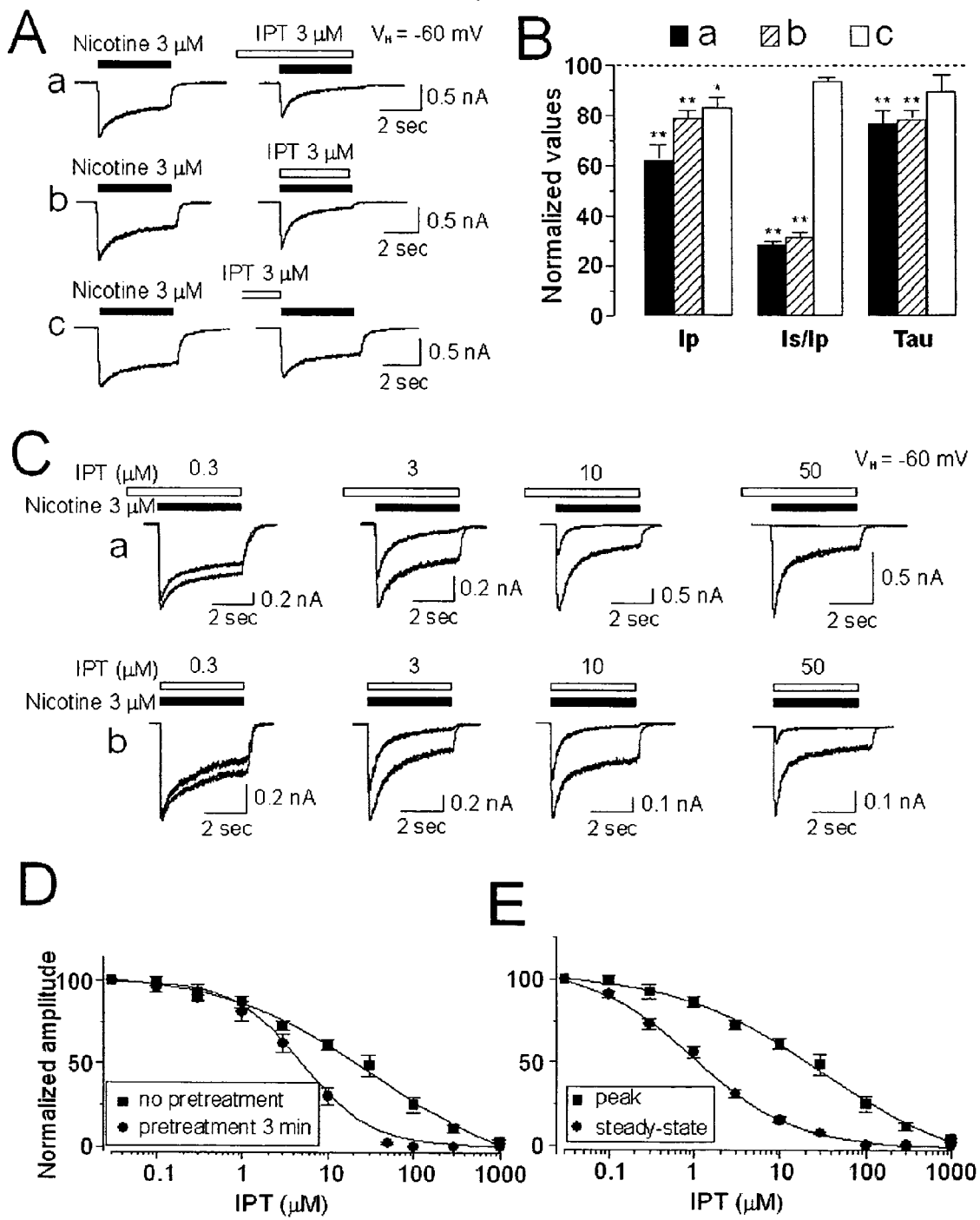
FIG. 4 illustrates the time- and dose-dependent effects of IPT on human $\alpha 4\beta 2$-nAChR function.

Initial time-dependence assays indicated that, compared to co-application, 3 min pretreatment with IPT produced a more profound inhibition of the response to 3 µM nicotine. FIG. 4A illustrates whole-cell current response traces for responses to 3 µM nicotine alone or in the presence of 3 µM IPT for 3 min prior to and then continuing during 4 sec agonist exposure (top traces), during agonist exposure only (middle traces), or following IPT pretreatment terminated at the time of agonist exposure (bottom traces).

Peak amplitudes of 3 µM nicotine-induced currents were reduced to 62±4% of control values following 3 min pretreatment followed by continued co-application with agonist plus IPT, to 79±9% without IPT pre-treatment but with co-application with nicotine, and to 81±7% following 3 min pre-treatment with IPT ending before exposure to nicotine alone. Steady-state:peak current amplitude ratios and the current decay time (τ) were lowest when IPT was co-applied with nicotine whether or not there was prior exposure to IPT.

FIG. 4B is a bar graph showing effects on 3 µM nicotine-evoked, peak whole-cell currents (Ip), the ratio between steady-state and peak currents (Is/Ip) or the whole-cell current decay constant (τ). All parameters are normalized to the value for responses to 3 μM nicotine alone (ordinate), under the pre- plus co-application condition (solid bars), the co-application condition (cross-hatched bars), or the pre-treatment condition alone (open bars). A single asterisk (*) represents p<0.05 and a double asterisk (**) represents p<0.01 compared to a 3 μM nicotine-induced current. Results are averages±SE from 6 cells.

Effects of IPT applied at different concentrations during a 4-sec nicotine exposure only or during nicotine exposure and after 3 min pre-treatment show concentration dependence of functional block as well as greater inhibitory efficiency after pre-treatment. FIG. 4C illustrates the effects on responses to 3 μM nicotine alone (higher amplitude, lighter shade traces) or with exposure to IPT at the indicated concentrations (lower amplitude, darker shade traces) are shown in representative traces for studies done after (Ca) 3 min pretreatment with IPT continuing during agonist application or (Cb) during co-application of IPT with agonist. To prevent complications due to long-lasting residual inhibition by IPT, each pre- and after-IPT exposure study was done using a different cell.

Concentration-response profiles for inhibition by IPT of peak whole-cell responses indicate $IC_{50}$ values of 5.0 and 31 μM with and without pretreatment with IPT, respectively. FIG. 4D illustrates the effects of the indicated concentration of IPT (abscissa, log μM scale) under the co-application (no pretreatment; ■) or 3 min pretreatment (●) conditions on peak current responses to 3 μM nicotine (ordinate, normalized amplitude; mean±SE, n=6 cells).

FIG. 4E illustrates that in co-application condition, the $IC_{50}$ value for IPT-mediated inhibition of the whole-cell steady-state current is 1.0 μM, which is lower than the $IC_{50}$ value for inhibition of the peak-component, (p<0.01, n=6). Specifically, FIG. 4E shows the concentration-inhibition relationships for effects of co-application with IPT at the indicated concentrations (abscissa, log μM scale) on peak (■) and steady-state (●) components (ordinate, normalized amplitudes; mean±SE, n=6 cells). The more profound inhibition after pre-treatment suggests that some IPT binding sites are accessible in the resting state.

Figure 5:
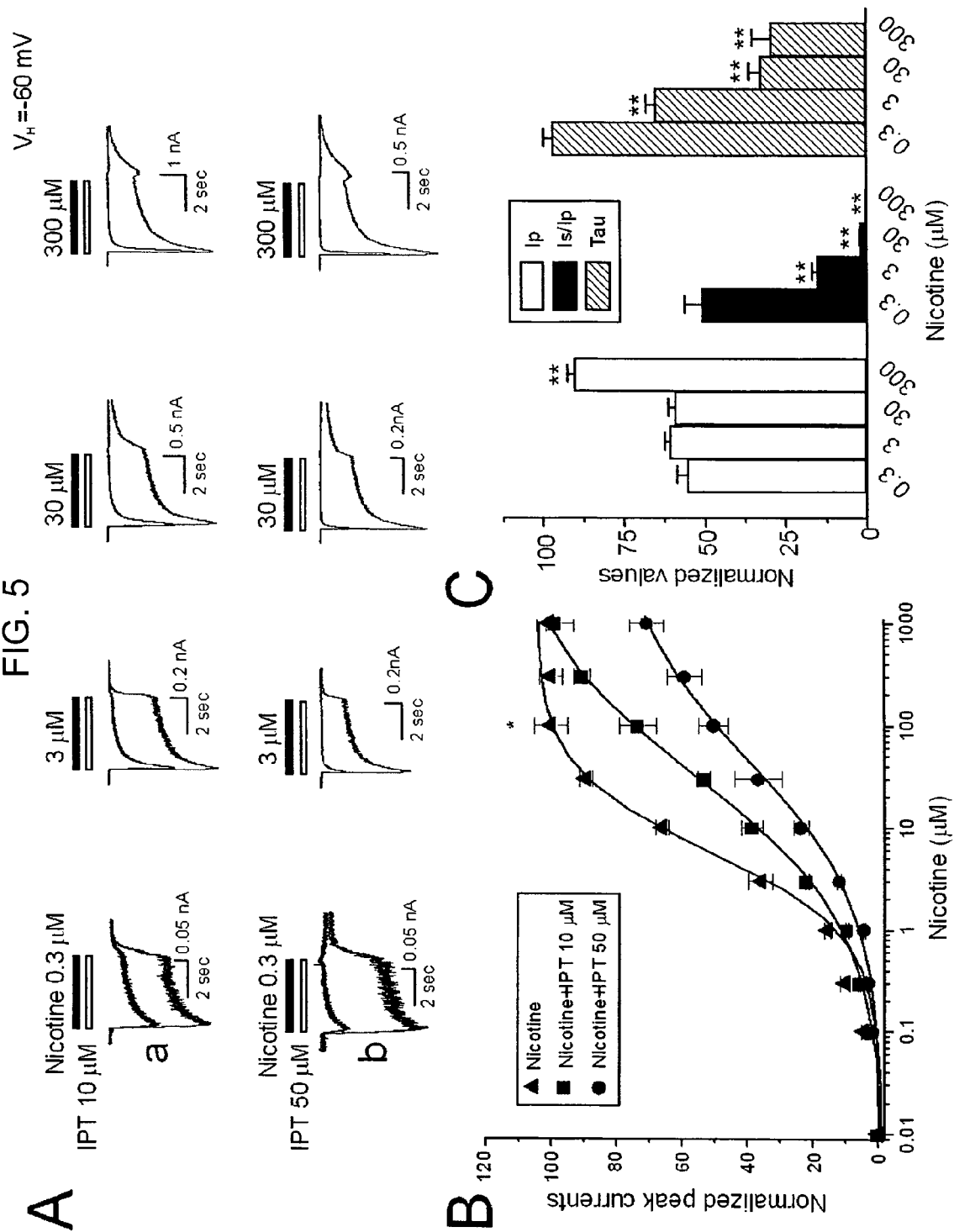
FIG. 5 shows the mechanism of how IPT block human $\alpha 4\beta 2$-nAChR function.

To explore the nature of IPT functional block, nicotine dose-response curves were obtained alone or in the presence of IPT at 10 or 50 μM from examination of whole-cell current traces as shown in FIG. 5A. Specifically, FIG. 5A shows representative whole-cell current traces for responses to nicotine alone (higher amplitude, lighter shade traces) or during co-application with 10 μM IPT (Aa) or 50 μM IPT (Ab) (lower amplitude, darker traces). These whole-cell current traces are shown for studies using a different cell for each agonist-alone and agonist-IPT pair.

As the concentration of co-applied IPT was increased, the nicotine $EC_{50}$ value for induction of whole-cell peak current increased from 5.1 μM to 21 and 102 μM in the nicotine alone, the presence of 10 and 50 μM IPT, respectively. This is illustrated in FIG. 5B which shows concentration-response curves for responses to nicotine at the indicated concentrations (abscissa, mean±SE for peak currents normalized to that in the presence of 100 μM nicotine alone*; n=6 cells; log μM scale) alone (▲), upon co-incubation with 10 μM IPT (■), or upon co-incubation with 50 μM IPT (●).

However, the Hill slope became progressively more shallow, and nicotine up to 1 mM was unable to surmount functional block by 50 μM IPT. Moreover, effects of 10 μM IPT on the amplitude of the steady-state current, on the ratio of the steady-state current to the peak current, and on the rate of acute desensitization quantified by the decay constant, τ, became enhanced as nicotine concentrations increased.

In FIG. 5C, the bar graph compares agonist concentration-dependence (abscissa; [nicotine] in μM) for effects of IPT on peak currents (Ip, open bars), the ratio of steady-state:peak currents (Is/Ip, closed bars), or the current decay constant (Tau, cross-hatched bars) normalized to the respective value in the presence of nicotine at the indicated concentration alone. A double asterisk (**) represents p<0.01 compared to a 0.3 μM nicotine-induced response.

Figure 6:
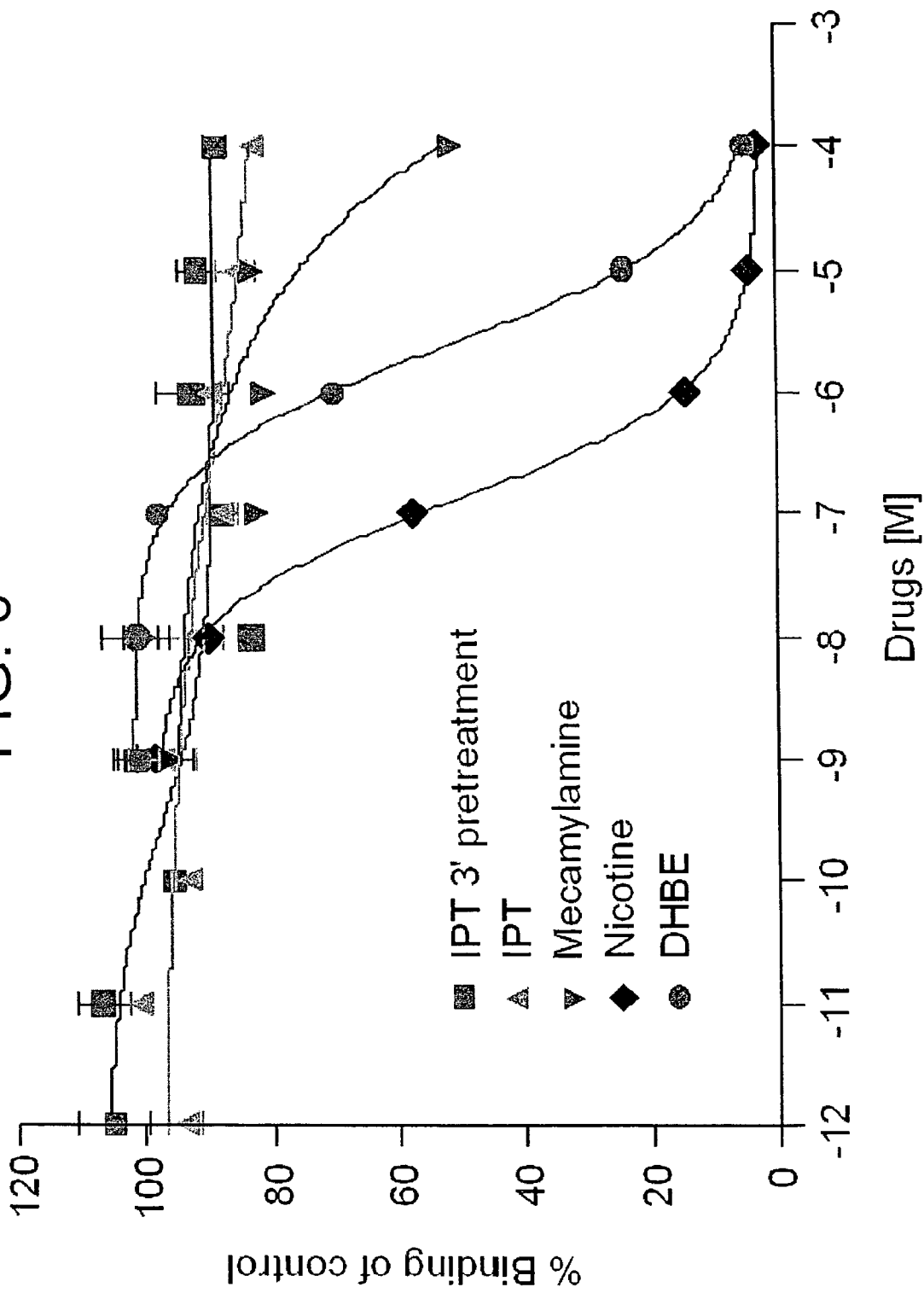
FIG. 6 shows that IPT does not act on $\alpha 4\beta 2$-nAChR agonist binding sites.

Referring now to FIG. 6, radioligand binding assays indicated that $^3$H-epibatidine binding was blocked by nicotine or dihydro-β-erythroidine with previously reported $IC_{50}$ values and that mecamylamine, a non-competitive inhibitor of α4β2-nAChR function, as well as IPT, failed to block radioligand binding at concentrations up to 1 mM. Collectively, these results suggest that IPT does not act on agonist binding sites (i.e., via a purely competitive mechanism) to exert its inhibition of α4β2-nAChR function.

Referring now to FIG. 7, when ionized ligands act to block ion channels, their residence in the transmembrane region is affected by trans membrane potential. Consequently, transmembrane voltage-dependence is one of the characteristic features of open-channel block by charged ligands. Whole-cell current responses to nicotine alone and in the presence of 50 μM IPT recorded at different holding potentials, as shown by the representative traces in FIG. 7A, indicate that IPT exerts stronger inhibition of nicotinic responses at more negative holding potentials, as shown in FIG. 7B.

In FIG. 7A, representative traces are superimposed for whole-cell current responses of SH-EP1-hα4β2 cells to 3 μM nicotine alone (larger amplitude, lighter shade traces) or during co-application with 50 μM IPT (lower amplitude, darker shade traces) at the indicated holding potentials ($V_H$). In FIG. 7B, voltage-dependent effects (abscissa) of co-application of 50 μM IPT with 3 μM nicotine on peak currents (closed bars) and the current decay constant (τ; open bars) are complied (ordinate; normalized to the value for the parameter in the presence of 3 μM nicotine alone; mean±SE; n=6 cells). A single asterisk (*) represents p<0.05 compared to a $V_H$=−80 mV.

Fractional inhibition by IPT of whole-cell peak current responses to nicotine was 80.9±2.65%, 76.4±2.6%, and 68.9±3.5% at holding potentials of −80, −40 and 0 mV, respectively, and current decay constants were 22±3.4%, 30±1.1%, and 44±7.6% of control, respectively, reaching significance for differences between $V_H$=−80 and 0 mV (p<0.05, FIG. 7B). These results indicate that effects on the α4β2-nAChR function of IPT are voltage-dependent.

As shown in FIG. 8, under conditions where whole-cell current responses of SH-EP1-hα4β2 cells to repetitive applications of nicotine for 4 sec at 3 min intervals showed no significant response rundown, 6 repetitive applications of nicotine (3 μM) in the continuous presence of 3 μM IPT resulted in a gradual reduction of nicotinic responses. However, as illustrated by FIG. 8A, after 15 min of IPT pre-treatment without repeated application of nicotine, there was less inhibition of a 3 μM nicotine-induced response than evident at the end of the repeated nicotine challenge protocol. In FIG. 8A SH-EP1 cells expressing α4β2-nAChRs were repetitively challenged with 3 μM nicotine (4 sec exposure at 3 min intervals) in the continuous presence of 3 μM IPT for 15 min (Aa) or nicotine was applied for 4 sec at the beginning and at the end of 15-min exposure to 3 μM IPT (Ab) comparing sets of responses recorded from different cells.

In FIG. 8B, a bar graph compares effects of IPT during repetitive exposure to nicotine (Aa; solid bars) or at the start and end of nicotine exposures (Ab, open bars) for whole-cell peak current responses (ordinate, normalized to responses in the absence of IPT) to nicotine at the onset (0 min) or at the end (15 min) of the IPT exposure period. A double asterisk (**) represents p<0.01 for the difference in effects assessed under the two different nicotine challenge protocols. As shown in FIG. 8B, a peak current amplitude in response to nicotine was reduced by the same amount (16.8±6.1%, 13.6±2.4%) after initial co-application of nicotine with IPT, but the response to the nicotine challenge after 15 min of 3 µM IPT exposure was only 11.9±1.7% of control after repeated nicotine challenges compared to 29.8±3.3% of control without them. These results indicate that IPT-mediated block of $\alpha4\beta2$-nAChR function is use-dependent.

Figure 9:
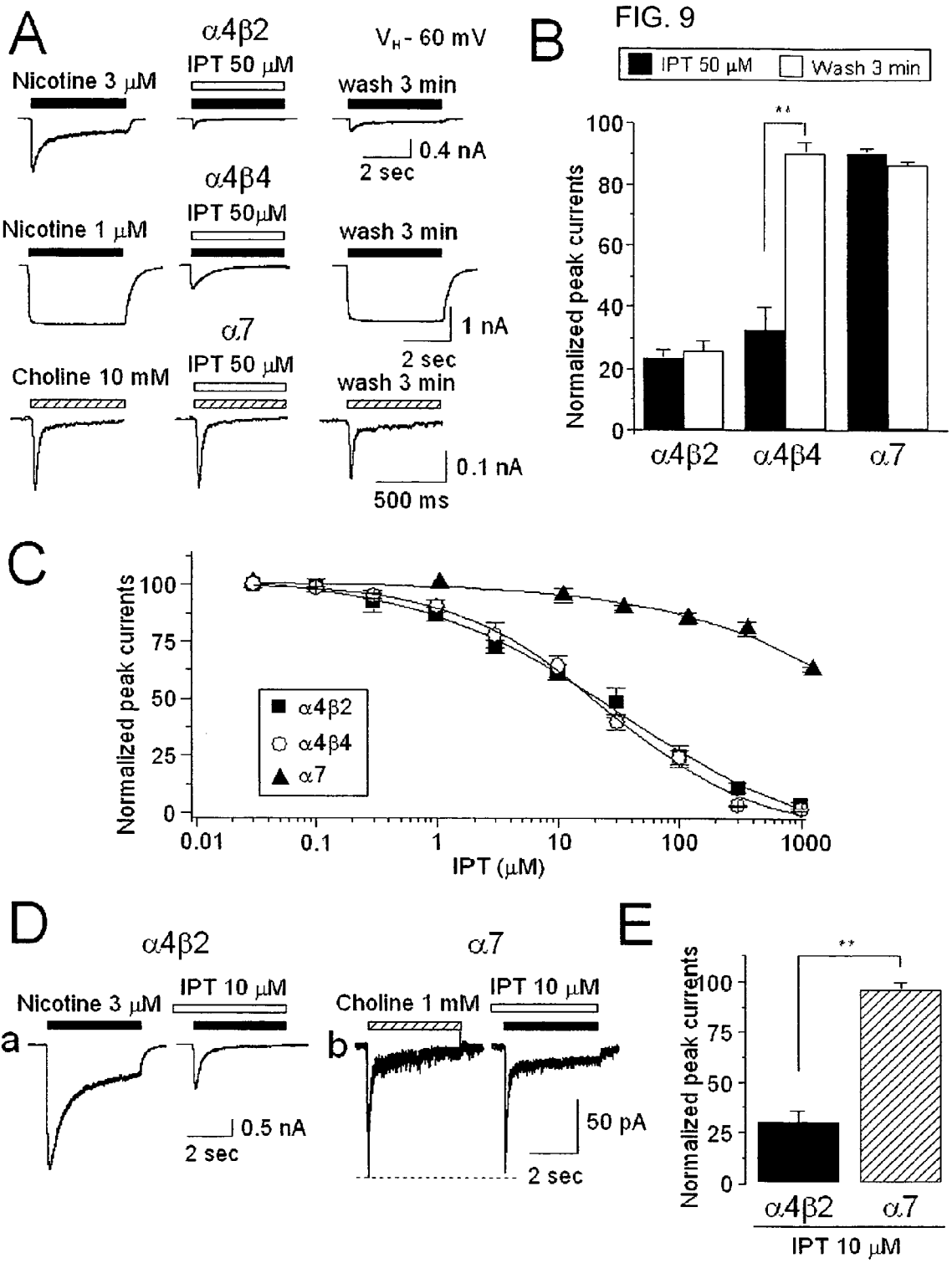
FIG. 9 shows the nAChR subtype selectivity of IPT-mediated inhibition.

FIG. 9 illustrates that IPT-mediated functional block persisted for $\alpha4\beta2$- but not $\alpha4\beta4$-nAChR after 3 min of drug washout. FIG. 9A shows representative whole-cell currents responses of $\alpha4\beta2$-nAChR to 3 µM nicotine, $\alpha4\beta4$-nAChR to 1 µM nicotine, or $\alpha7$-nAChR to 10 mM choline as indicated alone (as shown by the left trace in each row), in the presence of co-applied 50 µM IPT (as shown by the middle trace in each row), or after 3 min of IPT washout. FIG. 9B is a bar graph indicating extent of IPT-mediated inhibition of function (ordinate, normalized peak current responses to the challenge agonist alone as in A; mean±SE, n=6 cells) for the indicated nAChR subtype (abscissa) during co-application with agonist (50 µM IPT, solid bars) or after 3 min of drug washout (open bars).

FIG. 9C shows concentration-inhibition curves for IPT effects on peak current amplitudes demonstrate selective inhibition of $\alpha4$-containing nAChR function. FIG. 9C depicts the IPT concentration (abscissa; log µM scale) dependence of inhibition of function (ordinate; peak whole-cell current responses normalized to those in the absence of IPT; mean±SE, n=6 cells) of human $\alpha4\beta2$-(■), $\alpha4\beta4$-(○), or $\alpha7$- (▲) nAChR when IPT is co-applied with agonists.

As shown in FIG. 9D, $IC_{50}$ values of IPT for co-application with agonist were 31 and 23 µM, respectively, for $\alpha4\beta2$- and $\alpha4\beta4$-nAChR functional inhibition, but higher than 1 mM for $\alpha7$-nAChR blockade. FIG. 9D shows the representative whole-cell currents responses of (a) $\alpha4\beta2$-nAChR to 3 µM nicotine or (b) of $\alpha7$-nAChR to 1 mM choline as indicated alone (left traces) or after 3 min of pretreatment followed by continued exposure with agonist to 10 µM IPT (right traces).

Further, as shown in FIG. 9E, even at lower concentrations of choline (closer to its $EC_{50}$ value) for activation of $\alpha7$-nAChRs, and after 3 min pre-treatment of cells with 10 µM IPT, IPT exerted more profound inhibition of $\alpha4\beta2$-nAChR-mediated currents (70±11%) than of $\alpha7$-nAChR-mediated currents (3.5±0.4%). FIG. 9E is a bar graph indicating the extent of IPT-mediated inhibition of function (ordinate, normalized peak current responses to the challenge agonist alone as in D; mean±SE, n=6 cells) for $\alpha4\beta2$-nAChR (solid bar) responding to 3 µM nicotine or $\alpha7$-nAChR (cross-hatched bar) responding to 1 mM choline during 10 µM IPT pretreatment followed by co-application with agonist. A double asterisk (**) represents p<0.01.

The above results show that actions of IPT are nAChR subtype-selective, in that it is more potent as an antagonist of $\alpha4\beta2$- or $\alpha4\beta4$-nAChR than of $\alpha7$-nAChR, and its inhibitory effects are longer lasting at $\alpha4\beta2$- than at $\alpha4\beta4$-nAChR.

Figure 10:
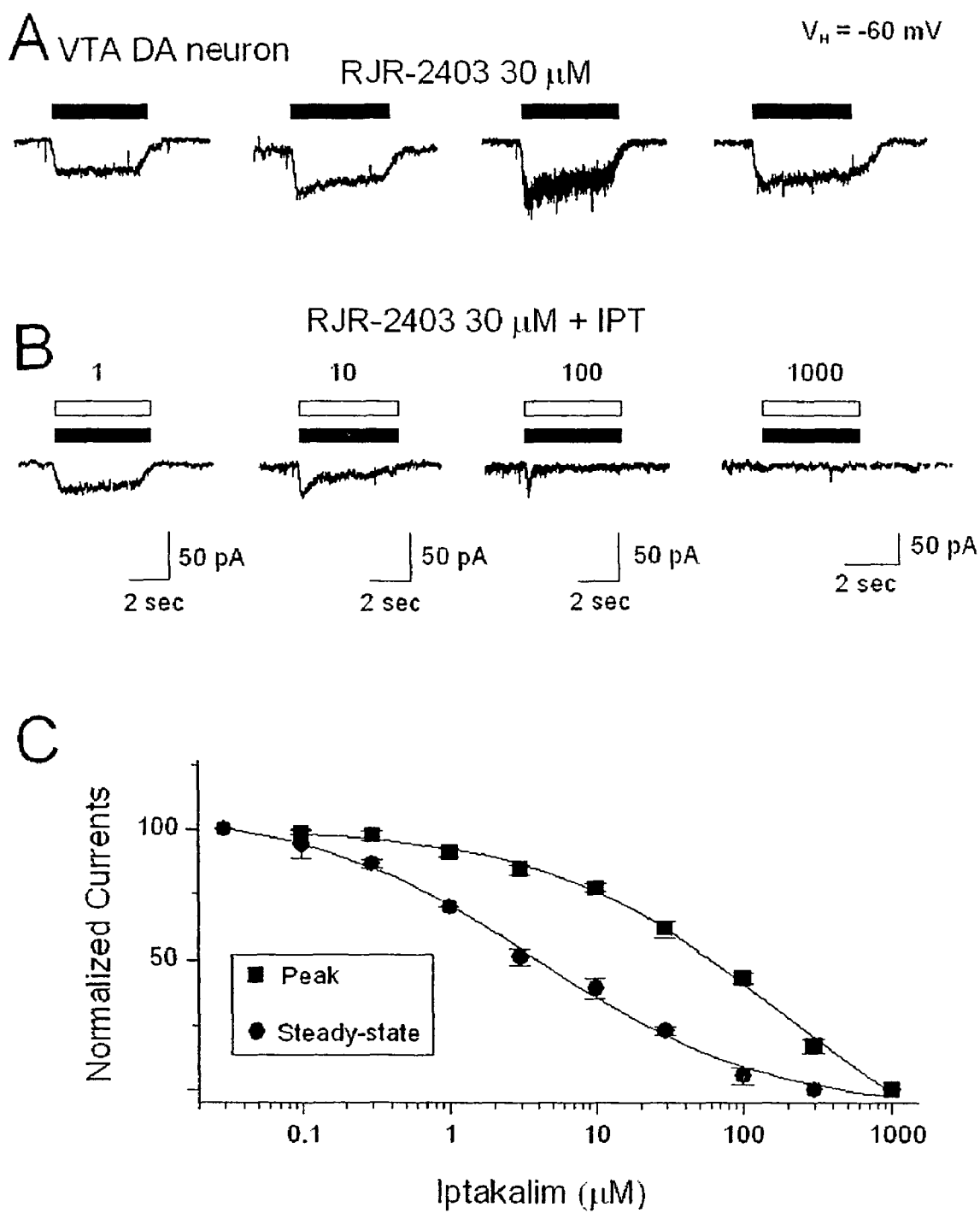
FIG. 10 illustrates the effects of IPT on native $\alpha 4\beta 2$-nAChR expressed in single dopamine neurons acutely dissociated from rat VTA.

Further, FIG. 10 shows the effects of IPT on native expressed $\alpha4\beta2$-nAChRs in single dopamine neurons acutely dissociated from rat VTA. FIG. 10 illustrates how typical traces representing four VTA DA neurons responded to $\alpha4\beta2$-nAChR selective agonist, RJR-2403 with (FIG. 10B) and without IPT (FIG. 10A). Specifically, FIG. 10A shows RJR-2403-induced inward current in four different VTA DA neurons. FIG. 10B illustrates that IPT inhibited RJR-2403-induced current response in a concentration-dependent manner. Finally, FIG. 10C summarizes the inhibition-efficacy relationship curves of IPT-induced inhibition in peak and steady-state currents.

Figure 11:
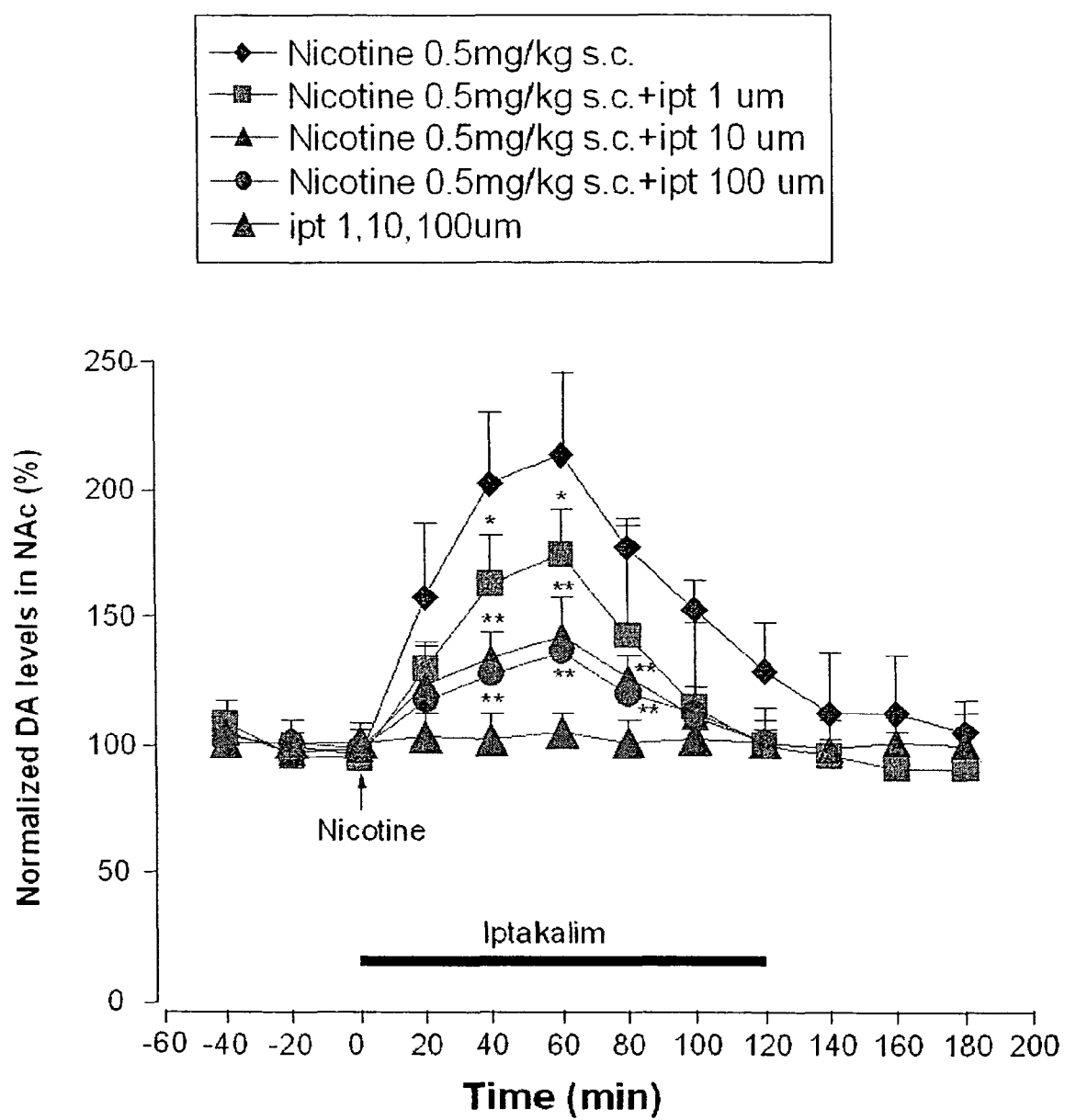
FIG. 11 shows the effects of IPT on the extracellular dopamine levels in the nucleus accumbens of acute nicotine administered rats.

Finally, the effects of IPT on the extracellular dopamine levels in the nucleus accumbens of acute nicotine-administered rats are illustrated by microdialysis. The results are shown in FIG. 11.

In the control group, a subcutaneous injection of nicotine (0.5 mg/kg) produced a significant increase in dopamine levels when compared with the final sample prior to nicotine administration, which produced a 100% increase. Local perfusion with IPT 1-100 µM from microdialysis probe, after subcutaneous injection of nicotine, tended to decrease nicotine-induced elevation of dopamine in the nucleus accumbens, and the differences were significant compared to rats receiving acute nicotine injection during the 20-80 minutes after nicotine injection. In FIG. 11, a single asterisk (*) represents p<0.05, and a double asterisk (**) represents p<0.01 for ANOVA, which was follow by a post hoc Dunnett's test, comparing individual time points with the nicotine 0.5 mg/kg control group.

These data illustrate a significant decrease in the extracellular dopamine levels in the IPT perfused rats, compared with the control group, and different doses of IPT (1-100 µM) produce effects on the extracellular dopamine levels in the nucleus accumbens of nicotine pretreated rats.

Through the mechanism illustrated above, IPT serves to reduce nicotine use and produce smoking cessation in humans through IPT-mediated block of $\alpha4\beta2$-nAChR function. IPT may have increased efficacy when combined with nicotine-replacement therapy (NRT). If IPT is used together with nicotine (either while still smoking or in conjunction with a nicotine additive or other nicotine-replacement therapy), the IPT will block the brain reward center function and reduce the reinforcement feeling, then gradually decrease the nicotine-dependence.

nAChR activation, desensitization, adaptation and/or up-regulation are thought to constitute the major cellular mechanisms underlying nicotine tolerance, dependence and withdrawal. It is thought that a major reason for failure in smoking cessation (quitting smoking) is the onset of nicotine withdrawal symptoms. An increase in numbers of nAChRs in the brain after long term exposure to nicotine could contribute to this. Once a human quits smoking, numerous nAChRs located on brain regions outside of the reward center will be activated by an endogenous nicotinic receptor agonist, acetylcholine, to produce a series cardiac, respiratory and endosecretary responses, called withdrawal symptoms.

Administration of IPT will decrease or eliminate withdrawal symptoms because IPT can also be used as a nAChR antagonist to block brain nAChR functions that are not located within brain reward center. Therefore, the optimal way to achieve smoking cessation is to block the brain reward center and block the over-expressed nAChR function. IPT can serve both functions and present a novel method to meet these needs, reducing nicotine use and sustaining smoking cessation.

The optimal dosage to decrease nicotine use and produce smoking cessation is by administering a dose of 3 mg/Kg of body weight of IPT, and the effects can be maintained up to 9 hours. The preferred dosage range is 1.0-4.0 mg/Kg body weight of IPT. However, because IPT compounds easily pass the blood-brain barrier, they quickly and easily reach peak concentration in the brain tissue. Therefore, doses as low as 0.5 mg/Kg of body weight can cause nAChRs blockade and decrease nicotine use. Also because of the ease in passing the blood-brain barrier, administration of IPT can be accomplished in several ways. Administration of IPT is effective when ingested orally, and numerous vehicles for delivery of IPT are possible. The method of administration of IPT includes preparation in forms of capsules, tablets, powders, liquids, chewing gum, tooth gel or paste, or food products.

The method of administration of IPT can also be by integrating it into sprays or lozenges to deliver sublingually to by-pass liver metabolism. The method of administration of IPT can also be by making IPT capable of respiratory inhalation. Administration of IPT can also be effectively accomplished by preparing the IPT in injectable forms to deliver parenterally to by-pass liver metabolism and for faster and stronger actions. IPT can be dissolved in injection solution and be prepared either for use as a subcutaneous injection or for use as a direct venous injection or intravenous solution. IPT can be prepared in suppository form and can be prepared in a form for administration by infusion pump.

Finally, IPT can be made into a patch so that the IPT can be administered by dermal application of the patch to the skin. A IPT patch can also be prepared with a nicotine additive, or other nicotine-replacement-therapy, for increased efficacy. The present disclosure envisions synthesizing the IPT compound as shown in FIG. 1 for use according to the present method.

Various embodiments of the invention are described above. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A method of treating nicotine craving or nicotine withdrawal symptoms in a living organism comprising the step of administering a therapeutically effective dose of iptakalim hydrochloride to the living organism.

2. The method of claim 1, wherein the therapeutically effective dose of iptakalim hydrochloride is an amount between about 0.5 milligrams and about 4 milligrams per kilogram of body weight of the living organism.

3. The method of claim 1, wherein the therapeutically effective dose of iptakalim hydrochloride is about 3 milligrams per kilogram of body weight of the living organism.

4. The method of claim 1, wherein nicotine use is decreased.

5. The method of claim 1, wherein the dose of iptakalim hydrochloride is administered orally.

6. The method of claim 5, wherein the dose of iptakalim hydrochloride is administered in a form selected from the group consisting of a liquid, a powder, a tablet, a chewing gum, a tooth gel, a tooth paste, and a food product.

7. The method of claim 1, wherein the dose of iptakalim hydrochloride is administered by via an administration route selected from the group consisting of sublingual, subcutaneous, intravenous and respiratory inhalation.

8. The method of claim 1, wherein the dose of iptakalim hydrochloride is administered as a suppository.

9. The method of claim 1, wherein the dose of iptakalim hydrochloride is administered by infusion pump.

10. The method of claim 1, wherein the dose of iptakalim hydrochloride is administered in a dermal patch.

11. The method of claim 10, further including the step of administering nicotine in the dermal patch.

12. The method of claim 1, wherein the dose of iptakalim hydrochloride is administered in a pharmaceutically acceptable carrier.

13. The method of claim 1, further including the step of administering nicotine-replacement therapy.

14. The method of claim 1, wherein the living organism is an animal.

15. The method of claim 14, wherein the living organism is a human.

16. A method of decreasing nicotine craving or nicotine withdrawal symptoms in a human comprising the step of administering a therapeutically effective dose of iptakalim hydrochloride to the human.

17. The method of claim 16, wherein the dose of iptakalim hydrochloride is administered in an amount about 0.5 milligrams and about 4 milligrams per kilogram of body weight.

18. The method of claim 16, further comprising the step of administering nicotine-replacement therapy.

19. The method of claim 16, wherein the dose of iptakalim hydrochloride is administered in a dermal patch.

20. The method of claim 19, further including administering nicotine in the dermal patch.

21. The method of claim 1 wherein treating of nicotine craving comprises deactivating nicotine receptors, reducing release of dopamine and blocking nicotine-activated brain reward center functions.

22. The method of claim 21 wherein the nicotine receptors are nAChR receptors.

* * * * *